(12) United States Patent
Birkenbach et al.

(10) Patent No.: US 10,292,775 B2
(45) Date of Patent: May 21, 2019

(54) SYSTEMS AND METHOD FOR DETERMINING THE SHAPE OF A SURGICAL INSTRUMENT AND SURGICAL INSTRUMENTS HAVING A DEFORMABLE BODY

(71) Applicant: Brainlab AG, Munich (DE)

(72) Inventors: Rainer Birkenbach, Erding (DE); Johannes Manus, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 16/146,514

(22) Filed: Sep. 28, 2018

(65) Prior Publication Data

US 2019/0029761 A1 Jan. 31, 2019

Related U.S. Application Data

(63) Continuation-in-part of application No. 14/238,767, filed as application No. PCT/EP2011/064689 on Aug. 26, 2011, now abandoned.

(51) Int. Cl.
*A61B 34/20* (2016.01)
*A61B 90/00* (2016.01)
*A61B 5/06* (2006.01)

(52) U.S. Cl.
CPC .............. *A61B 34/20* (2016.02); *A61B 90/06* (2016.02); *A61B 5/065* (2013.01);
(Continued)

(58) Field of Classification Search
CPC . A61B 34/20; A61B 90/06; A61B 2034/2051; A61B 2034/2061; A61B 2090/061; A61B 2090/064; A61B 5/065
See application file for complete search history.

(56) References Cited

U.S. PATENT DOCUMENTS 5,274,551 A * 12/1993 Corby, Jr. .............. A61B 6/463
348/45
5,781,681 A 7/1998 Manning
(Continued)

FOREIGN PATENT DOCUMENTS

DE 102009021705 A1 11/2010
EP 2233099 9/2010

OTHER PUBLICATIONS

Dobrokhotov et al., 2008, Visual force sensing with flexible nanowire buckling springs, Nanotechnology 19, 035502 (Year: 2008).*
(Continued)

*Primary Examiner* — Bo Joseph Peng
(74) *Attorney, Agent, or Firm* — Tucker Ellis, LLP (57) ABSTRACT

A system and method for determining the spatial position and the shape of a surgical instrument (1) having a deformable body (2) by: providing an elasticity model of the surgical instrument (1); defining at least one parameter which influences the shape of the instrument (1); determining the spatial position and/or orientation of at least one tracking sensor (3) of the surgical instrument (1); determining the value of the at least one parameter; calculating the position and/or orientation of at least one part of the surgical instrument (1) with the aid of the elasticity model together with the determined value of the at least one parameter and the determined spatial position and/or orientation of the at least one tracking sensor (3). The present invention also relates to a surgical instrument (1) having a deformable body (2) comprising at least two sensors (3, 4), wherein at least one sensor is a tracking sensor (3) and at least one other sensor is a sensor (4) which allows the value of a predetermined parameter influences the shape of the instrument (1) to be determined.

20 Claims, 4 Drawing Sheets

(52) U.S. Cl.
CPC ............... *A61B 2034/2051* (2016.02); *A61B 2034/2061* (2016.02); *A61B 2090/061* (2016.02); *A61B 2090/064* (2016.02)

(56) References Cited

U.S. PATENT DOCUMENTS

| | | | |
|---|---|---|---|
| 7,194,296 B2 | 3/2007 | Frantz et al. | |
| 7,292,966 B2 | 11/2007 | Nailo | |
| 7,695,197 B2 | 4/2010 | Gurreri | |
| 2003/0229279 A1 | 12/2003 | Amstutz et al. | |
| 2004/0064015 A1* | 4/2004 | Goto | A61B 1/012 600/104 |
| 2005/0256398 A1* | 11/2005 | Hastings | A61B 34/73 600/423 |
| 2007/0106114 A1* | 5/2007 | Sugimoto | A61B 1/31 600/117 |
| 2008/0139916 A1* | 6/2008 | Maier | A61B 90/36 600/407 |
| 2008/0171934 A1 | 7/2008 | Greenan et al. | |
| 2009/0082216 A1* | 3/2009 | Cohn | B82Y 40/00 506/9 |
| 2009/0304245 A1* | 12/2009 | Egger | A61F 2/82 382/128 |
| 2010/0056904 A1 | 3/2010 | Saunders et al. | |
| 2010/0191056 A1* | 7/2010 | Tanaka | A61B 1/005 600/117 |
| 2011/0295111 A1* | 12/2011 | Hansis | A61B 90/39 600/424 |
| 2011/0319714 A1* | 12/2011 | Roelle | A61B 1/00006 600/118 |
| 2012/0136626 A1 | 5/2012 | Mucha | |

OTHER PUBLICATIONS

European Patent Office, International Search Report and Written Opinion for international application No. PCT/EP2011/064689 dated May 22, 2012; pp. 1-7.

* cited by examiner

SYSTEMS AND METHOD FOR DETERMINING THE SHAPE OF A SURGICAL INSTRUMENT AND SURGICAL INSTRUMENTS HAVING A DEFORMABLE BODY

CROSS REFERENCE TO RELATED APPLICATIONS

This application is a continuation-in-part of U.S. application Ser. No. 14/238,767, filed Apr. 28, 2014, which is the US National Stage of International Application No. PCT/EP2011/064689, filed Aug. 26, 2011, the contents of each of which are incorporated herein by reference in their entireties.

TECHNICAL FIELD

The embodiments herein relate generally to tracking of surgical instruments and to surgical instruments having bodies that may be tracked. More specifically, particular embodiments relate to a surgical instrument having a deformable body the spatial position and/or shape of which is trackable, and to methods for determining or otherwise monitoring the spatial position and/or shape of the deformable body and/or of a working portion of the deformable body of the surgical instrument by indirect observation.

BACKGROUND

In the field of surgical tracking technology, electromagnetic (EM) tracking technology provides the ability to track very tiny sensors which can be integrated in medical instruments. Thus, even very small instruments such as for example catheters can be tracked inside a patient's body into which they have been introduced. However, the number of sensors which can be placed in the instrument is very limited. The number of channels an EM tracking system can track simultaneously is restricted, as is the space available for placing the sensors and their cabling in the instrument. For these reasons, it is typically the case that only a few parts of the instrument to be tracked are provided with a tracking sensor. One tracking sensor is for example placed in the tip of a catheter, such that only the position of the tip of the catheter can be tracked. The shape of the catheter remains undisclosed to the user.

U.S. Pat. Pub. No. 2012/0136626 to Mucha teaches a system and method for determining the shape of a surgical instrument such as a catheter. However, the system taught there requires the use of a plurality of sensors disposed along the length of a working portion of the catheter. This unfortunately renders the catheter design somewhat thicker than standard non-trackable catheters having otherwise equivalent medical characteristics, and somewhat heavier than standard non-trackable catheters having otherwise equivalent medical characteristics.

It is an object of the example embodiments of the claimed invention to provide a solution to the aforementioned problems. In particular, the example embodiments aim to enable the shape of an instrument, in particular the overall shape of an instrument having a limited number of tracking sensors, in particular only one tracking sensor, to be determined. It is another object of the example embodiments of the claimed invention to provide a corresponding instrument having a limited number of tracking sensors, in particular only one tracking sensor, wherein the shape of at least part of the instrument but in particular the overall shape of the instrument can be determined by tracking the available tracking sensors.

In particular, the example embodiments, replacing all of the tracking sensors except the one at the tip with a, for example, bending stress sensor helps in providing a slimmer and leaner trackable catheter.

In general, therefore, and in accordance with the example embodiments, a method is provided for determining the shape of a surgical instrument having a deformable body. The method of the example embodiment described herein includes steps comprising providing an elasticity model of an associated surgical instrument, and defining at least one parameter which influences the shape of the associated instrument. The method of the example embodiment further determines the spatial position and/or orientation of at least one tracking sensor of the surgical instrument, and determines the value of the at least one parameter. The method of the example embodiment still further calculates the position and/or orientation of at least one part of the associated surgical instrument using an elasticity model based on the determined value of the at least one parameter and the determined spatial position and/or orientation of the at least one tracking sensor.

SUMMARY OF THE EXAMPLE EMBODIMENTS

The embodiments herein provide for new and improved systems and methods for determining the shape of an associated surgical instrument.

In the embodiments herein, the systems and methods determine the shape of an associated surgical instrument using a set of one or more position and/or tracking sensor(s) placed on the associated surgical instrument.

In the embodiments herein, the systems and methods determine the shape of an associated surgical instrument using a set of one or more force and/or tension sensor(s) coupled with the associated surgical instrument.

In embodiments herein, systems and methods are provided, wherein the above objects are achieved by a method in a system including a processor and a memory device operatively coupled with the processor for determining the spatial position and the shape of an elongated deformable body of an associated surgical instrument. The method includes storing a predefined elasticity model of the elongated deformable body in the memory device. In the embodiment the predefined elasticity model describes deformation of the elongated deformable body of the associated surgical instrument as a function of: i) a spatial position and orientation of a tip of the elongated deformable body of the associated surgical instrument; and ii) an influence on the elongated deformable body of the associated surgical instrument by at least one parameter. The method further includes determining by a tracking sensor disposed at the tip of the deformable body of the associated surgical instrument, a measured spatial position and orientation of the tip of the elongated deformable body. The method still further includes determining the at least one parameter by a physical parameter sensor operatively coupled with the associated surgical instrument. Further in the method, logic stored in the memory device is executed by the processor to calculate the spatial position and the shape of an elongated deformable body of an associated surgical instrument based on applying: i) the at least one parameter determined by the physical parameter sensor; and ii) the measured spatial position and orientation of the tip of the elongated deformable body determined by the tracking sensor to the predefined elasticity model of the elongated deformable body in the memory device.

In embodiments herein, a method is provided in a system including a processor and a memory device operatively coupled with the processor for determining the spatial position and the shape of an elongated deformable body of an associated surgical instrument. The method includes storing a predefined elasticity model of the elongated deformable body in the memory device. In the embodiment the predefined elasticity model describes deformation of the elongated deformable body of the associated surgical instrument as a function of: i) a spatial position and orientation of a tip of the elongated deformable body of the associated surgical instrument relative to a mid-proximal location of the elongated deformable body spaced from the tip by a distance s along the body of the associated surgical instrument; and ii) an influence on the elongated deformable body of the associated surgical instrument by at least one parameter. The method further includes determining by a tracking sensor disposed at the tip of the deformable body of the associated surgical instrument, a measured spatial position and orientation of the tip of the elongated deformable body relative to the mid-proximal location of the elongated deformable body. The method still further includes determining the at least one parameter by a physical parameter sensor operatively coupled with the associated surgical instrument. Further in the method, logic stored in the memory device is executed by the processor to calculate the spatial position and the shape of an elongated deformable body of an associated surgical instrument based on applying: i) the at least one parameter determined by the physical parameter sensor; and ii) the measured spatial position and orientation of the tip of the elongated deformable body relative to the mid-proximal location of the elongated deformable body determined by the tracking sensor to the predefined elasticity model of the elongated deformable body in the memory device.

Further in embodiments herein, a trackable surgical instrument is provided. The surgical instrument includes an elongate flexible body. A tracking sensor is disposed at a tip of the deformable body, the tracking sensor determining a measured spatial position and orientation of the tip of the elongate flexible body. A physical parameter sensor is operatively coupled with the elongate flexible body, the physical parameter sensor determining at least one parameter of the elongate flexible body of the surgical instrument. The spatial position and/or shape of the elongate flexible body is determinable using a predefined elasticity model of the elongate flexible body, wherein the predefined elasticity model describes deformation of the elongate flexible body of the surgical instrument as a function of: i) the measured spatial position and orientation of the tip of the elongated deformable body; and ii) an influence on the elongate flexible body of the surgical instrument by the at least one parameter of the elongate flexible body of the surgical instrument.

In yet further embodiments herein, a system is provided. The system includes a surgical instrument, a tracking sensor, a physical parameter sensor, a processor, and a memory device storing a predefined elasticity model and logic. The surgical instrument comprises an elongate flexible body. The tracking sensor is disposed at a tip of the elongate flexible body and determines a measured spatial position and orientation of the tip of the elongate flexible body. The physical parameter sensor is operatively coupled with the elongate flexible body and determines at least one parameter of the elongate flexible body of the surgical instrument. The memory device is operatively coupled with the processor. The predefined elasticity model of the elongate flexible body stored in the memory device describes deformation of the elongate flexible body of the associated surgical instrument as a function of: i) a spatial position and orientation of a tip of the elongate flexible body of the associated surgical instrument; and ii) an influence on the elongate flexible body of the associated surgical instrument by at least one parameter. The logic stored in the memory device is executable by the processor to calculate the spatial position and the shape of an elongate flexible body of an associated surgical instrument based on applying: i) the at least one parameter determined by the physical parameter sensor; and ii) the measured spatial position and orientation of the tip of the elongate flexible body determined by the tracking sensor to the predefined elasticity model of the elongate flexible body in the memory device.

Other embodiments, features and advantages of the example embodiments will become apparent from the following description of the embodiments, taken together with the accompanying drawings, which illustrate, by way of example, the principles of the example embodiments.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to exemplify the embodiments of this invention.

DETAILED DESCRIPTION OF THE EXAMPLE EMBODIMENTS

In the following description of the present invention reference is made to the accompanying figures which form a part thereof, and in which is shown, by way of illustration, exemplary embodiments illustrating the principles of the present invention and how it is practiced. Other embodiments can be utilized to practice the present invention and structural and functional changes can be made thereto without departing from the scope of the present invention.

Figure 1:
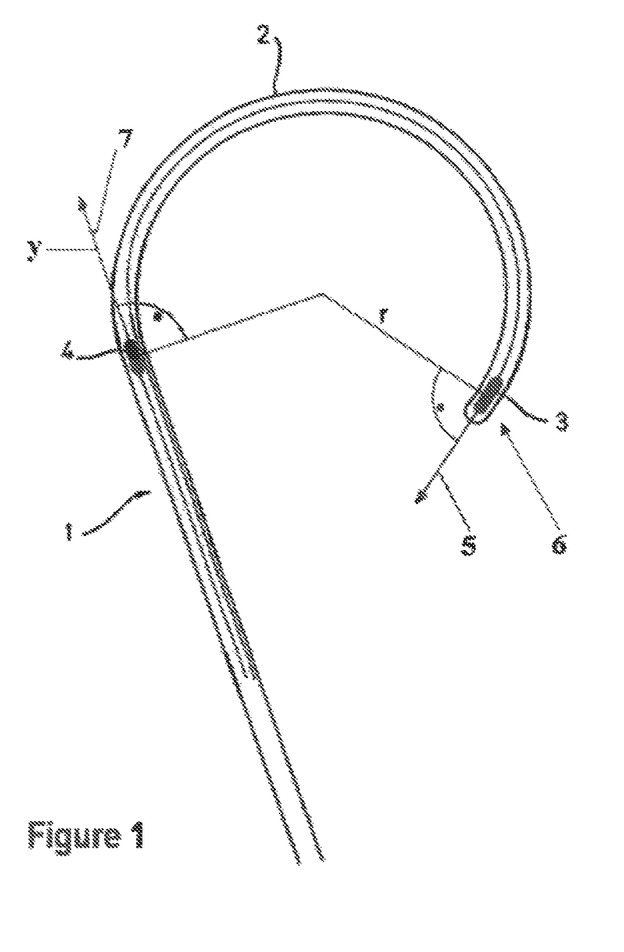
FIG. 1 shows an associated surgical instrument in the form of an elongated catheter having a body with a lower, rigid section and an upper, deformable (for example an elastic or a plastic) section, and carrying a pair of position and/or tracking sensors in accordance with an example embodiment.

Referring now to the drawings, wherein the showings are for the purpose of illustrating example embodiments only, and not for purposes of limiting the same, FIG. 1 shows an elongated catheter 1 having a body 2 with a lower, rigid section and an upper, deformable (for example an elastic or a plastic) section. Two sensors 3, 4 are integrated in the catheter 1 and/or catheter body 2, wherein the sensor 3 is an EM tracking sensor placed at the tip of the catheter and the sensor 4 is also an EM tracking sensor. The spatial position and orientation of both sensors 3 and 4 can be determined by means of an EM tracking system. Arrows extending from the sensors 3 and 4 indicate the tangential direction of the catheter body 2 and the position of the sensors 3 and 4.

Since the material properties do not change in the deformable section between the sensors 3 and 4, pulling a pull-wire 5 attached to the tip 6 of the catheter out of the proximal end 10 of the catheter 1 will cause a uniform deformation of the catheter body 2 between the sensors 3 and 4.

Since the material properties as well as the geometric properties of the deformable body section are known, an elasticity model of the instrument can be provided, wherein the shape of the deformable body section can be calculated with the aid of the elasticity model, and the spatial position and orientation of the catheter parts in which the sensors 3 and 4 are placed can be calculated from the measured position and orientation of the sensors 3 and 4 by means of an EM tracking system.

The overall shape of the catheter 1 can thus be calculated using only two EM sensors.

In other words, the elasticity model that is provided of the instrument defines how the instrument deforms under the influence of certain parameters such as for example force, pressure, stress or the like. Parameters are defined which influence the shape of the instrument. For example, a force acting transversely on the tip of the instrument body will cause the instrument body to bend. The greater the force, the greater the deflection. Therefore, the value of the defined parameters are also provided. Once the nature and magnitude of deformation in the shape of the instrument as a function of certain parameters and their value has been ascertained, the actual shape of the instrument calculated in accordance with the example embodiment from the elasticity model of the surgical instrument and the parameters, and their value, acting on the surgical instrument.

The expression "deformable body" as used herein is to be understood as describing a body which is deformable, irrespective of whether the body, once deformed, will return to its original shape automatically (elastic body) or will keep its shape, providing no further influence acts on it. In other words, the deformable body can act as a resilient body, such as for example a spring, or a ductile body, such as for example a modelling material (plastic body). Moreover, the body can be an elastic body or a plastic body.

It is to be appreciated that the sensors 3, 4 need not both be EM sensors. In an example embodiment. By determining the spatial position and/or orientation of at least one tracking sensor of the surgical instrument, the spatial position and/or orientation of at least one point of the surgical instrument is known.

Since the spatial position and/or orientation of at least one point of the surgical instrument is known, and the geometric properties, particularly including the cross-sectional shape of the instrument are known, the position and/or orientation of at least one part of the surgical instrument can be calculated with the aid of the elasticity model of the instrument, by inputting the values for the spatial position and/or orientation of the at least one tracking sensor and the determined value of the at least one parameter into the elasticity model.

For example, the shape of the instrument can be described by a simple parameterised function dependent on a number of parameters $a_j$, wherein every point on the instrument $x_i^0$ can be calculated by the function:

$$x_i = f(i; a_1, \ldots, a_n).$$

If m tracking sensors are placed in the instrument, the position and/or orientation of m points of the instrument are known by determining the position and/or orientation of said m sensors. Consequently, a system of m equations can be established:

$$x_1 = f(1; a_1, \ldots, a_n).$$

$$\ldots$$

$$x_m = f(m; a_1, \ldots, a_n).$$

This system of equations can then be solved for the parameter $a_j$ using a standard equation solver. The position of every point of the instrument can then be calculated using the function together with the known parameters $a_j$.

The above embodiment can be applied to instruments which exhibit simple geometries, for example a catheter comprising a tubular body.

More specifically, the implementation of the solution of the system of equations above will be demonstrated below in accordance with an example embodiment.

With continued reference to FIG. 1 and without loss of generality it may be assumed that a coordinate system is selected in which the sensors 3, 4, lie in the plane z=0 of an x, y, z orthogonal coordinate space. It may further be assumed that sensor 4 is at the coordinate origin 0, 0, 0 and that the axis 7 of the sensor 4 extends along the y axis. The first sensor 3 is disposed at the tip 6 of the elongated deformable body of the surgical instrument 1 relative to a mid-proximal location of the sensor 4 carried on the elongated deformable body spaced from the tip by a distance s along the body of the associated surgical instrument and along the x axis by an amount to be determined in accordance with a bending force applied to the tip relative to the working portion between the tip and the mid-proximal location. The transformation into this coordinate system is calculated from the position and orientation of sensors 3 and 4 in accordance with the example embodiment as described below in particular.

The elastic model for this case is that the catheter between sensor 4 and 3 describes a circular section of length s. This means that the exact shape of the catheter can be described as a parameterized curve with a form parameter $\alpha \in ]0, 2\pi]$ and the running parameter t (Equation 1):

$$(x; y)(t) = \left(\frac{s}{\alpha}(1 - \cos t); \frac{s}{\alpha} \sin t\right) \text{mit } t \in [0; \alpha]$$

The path length of this parameterized curve is always s which is already implicitly fulfilled.

The system of equations $$x_1 = f(1; a_1, \ldots, a_n).$$

$$\ldots$$

$$x_m = f(m; a_1, \ldots, a_n).$$

described above for the position of the sensors wherein the second sensor 4 is already at the coordinate origin, sensor 3 corresponds to the tip of the catheter is then (Equation 2):

$$(x; y)_{S3} = \left(\frac{s}{\alpha}(1 - \cos \alpha); \frac{s}{\alpha}\sin \alpha\right)$$
$$(x; y)_{S4} = (0, 0)$$

Figure 2:
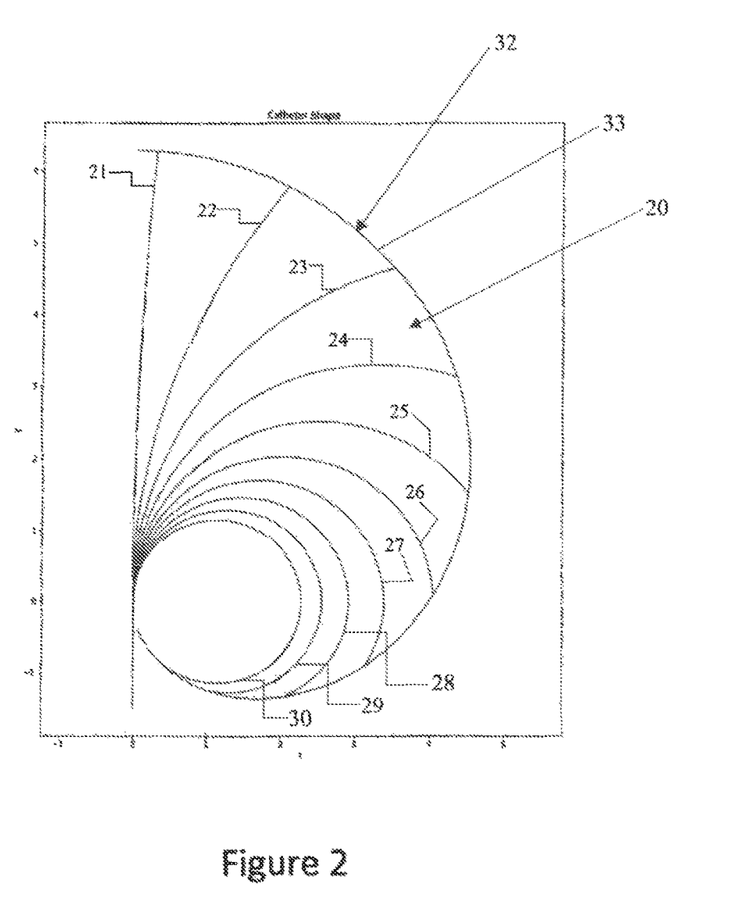
FIG. 2 shows a set of catheters moved through a series of bends in reaction to an influencing energy such as a force, pressure, and/or stress/strain illustrating the arc followed by the tip of the catheter as the working portion is moved through the series of bends and showing a range of shapes of the working portion moved in conformance with the applied energy.

FIG. 2 shows a set of catheters moved through a series of bends in reaction to an influencing energy such as a force, pressure, and/or stress/strain illustrating the arc followed by the tip of the catheter as the working portion is moved through the series of bends and showing a range of shapes of the working portion moved in conformance with the applied energy. In this Figure the shape of the catheter for different values of a is shown graphically as a set 20 of lines 21-30 according to Equation 1 above, wherein the envelope 32 of all possible positions of the tip is shown as a line 33 having a nautilus shape (according to equation 2/1). If the position of sensor 3 is now determined by measurement, sensor 3 will be on or near the line 33. The system of equations can now be solved (e.g. in the sense of smallest error squares, since the tip will not lie exactly on the line 33 due to measurement uncertainties) and thus the parameter a can be determined. This determines the entire shape of the catheter (one(s) of the lines 21-30).

It is to be appreciated that more complex instruments may not be able to be described by a simple function dependent on a small number of parameters. In this case, a finite elements algorithm may be applied. In this example embodiment, the instrument is modelled on the basis of its physical properties, and a finite elements algorithm may further be used to calculate the shape of the instrument, such that the position of every point of the instrument is known. Additionally, the determined position and/or orientation of the sensors can be used to determine the correct boundary conditions for the finite elements calculation.

In accordance with an example embodiment of the claimed invention, the tracking sensor is an electromagnetic (EM) tracking sensor, wherein the position and/or orientation of the tracking sensor is determined by an electromagnetic (EM) tracking method.

In accordance with a further example embodiment the spatial position and the shape of an elongated deformable body of an associated surgical instrument is determined in accordance with a predefined elasticity model of the elongated deformable body based on a spatial position and orientation of the tip of the elongated deformable body relative to the mid-proximal location of the elongated deformable body measured by a sensor on the tip of the body and based on an influence on the elongated deformable body of the associated surgical instrument by at least one parameter measured using a second sensor that is not a position sensor. In the example embodiment, the second sensor measures one or more of a force applied to the tip of the elongate body relative to a proximal portion of the body by a force sensor, a pressure applied to the tip of the elongate body relative to a proximal portion of the body by a pressure sensor; and/or parameter a stress applied to the tip of the elongate body relative to a proximal portion of the body by a force sensor.

Figure 3:
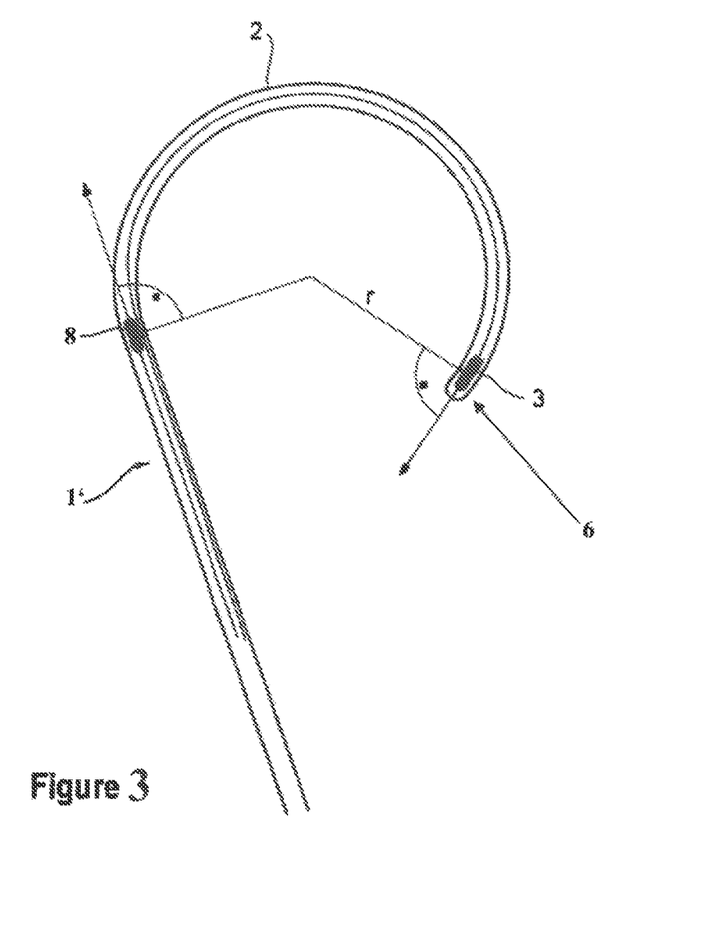
FIG. 3 shows an associated surgical instrument in the form of an elongated catheter having a body with a lower, rigid section and an upper, deformable (for example an elastic or a plastic) section, and coupled with a force and/or tension sensor in accordance with an example embodiment.

In connection with this example embodiment and with reference next to FIG. 3, the value of the at least one predetermined parameter is determined by means of a sensor 8, in particular a sensor which is placed in the surgical instrument. Such a sensor 8 may be configured to measure a distance, force, pressure and/or stress or any other suitable parameter which can cause the surgical instrument to be deformed.

In accordance with the example embodiment, the spatial position and the shape of an instrument having only one EM sensor 3 is determined, wherein the EM sensor 3 is placed at the tip 6 of the instrument 1, and the additional information of the instrument is obtained from another sensor 8 which is not a tracking sensor. In one example, the sensor 8 measures a force acting on the instrument 1. In another example, the sensor 8 measures a bending of or stress within the instrument body 1. In another example, the sensor 8 measures the length of a pull-wire 5 of a catheter which is pulled in order to change the shape of the catheter. In a further example embodiment, the sensor 8 measures one or more of a force acting on the instrument 1, a bending/stress acting on the instrument 1, and/or the length of a pull-wire 5 of a catheter which is pulled in order to change the shape of the catheter.

Generally, any sensor which provides information for calculating the shape of the surgical instrument can be used.

The method of the present invention can also be used to calculate the shape of two-dimensional structures such as electrode grid sheets used for cortical stimulation and mapping. The position of the electrodes could be calculated by assimilating the shape of the electrode grid sheet as determined on the basis of the measurements of a number of tracking sensors attached to the sheet.

It is also possible to determine the value of more parameters than is necessary for calculating the shape of the instrument, in order to provide a reliability measurement, such that distortions in the EM tracking system and potential tracking inaccuracies can be detected. Field distortions caused by ferrous or conductive materials can therefore be detected and the user warned.

In accordance with another preferred embodiment of the present invention, not only the position and/or orientation of at least one part of the surgical instrument but rather the overall shape of the instrument is calculated. This allows the overall shape of the instrument to be displayed on a display device 450 (FIG. 4) in a user-friendly manner within a medical navigation method. The user can then see the whole instrument in its actual shape in relation to other surgical data such as in particular images of the patient.

Another aspect of the present invention relates to a program which, when running on a computer or loaded onto a computer, causes the computer to perform a method as described above. Another aspect of the present invention relates to a program storage medium in which the above program is stored.

Another aspect of the present invention relates to a surgical instrument which has a deformable body and at least two sensors, wherein at least one sensor is a tracking sensor and at least one other sensor is a sensor which provides additional information for calculating the shape of at least one part of the surgical instrument, namely by determining the value of a predetermined parameter which influences the shape of the instrument. However, it is possible for the at least one other sensor to also be a tracking sensor, in particular an EM tracking sensor. The at least one other sensor can however be configured to measure a distance, force, pressure, stress or any other parameter which influences the shape of the surgical instrument.

In FIG. 3, the EM tracking sensor 4 is replaced with a physical parameter sensor which is not an EM tracking sensor. For example, a sensor could be provided which measures the amount of pull-wire which is pulled out of the proximal end of the catheter 1, so as to obtain information on the extent to which the deformable part of the catheter body 2 will deform. Such a sensor could also be provided outside of the catheter body 2, such that the catheter 1 only comprises one EM tracking sensor and can therefore be designed even smaller.

With continued reference to FIG. 3 and without loss of generality it may be assumed that a coordinate system is selected in which the sensor 3 lies in the plane z=0 of an x, y, z orthogonal coordinate space. It may further be assumed that the first sensor 3 is disposed at the tip 6 of the elongated deformable body of the surgical instrument 1 relative to a mid-proximal location of the elongated deformable body spaced from the tip by a distance s along the body of the associated surgical instrument and along the x axis by an amount to be determined in accordance with a bending force applied to the tip relative to the working portion between the tip and the mid-proximal location. The transformation into this coordinate system is calculated from the position and orientation of sensor 3 and a parameter that operates to bend the body of the instrument in accordance with the example embodiment as described below in particular.

The elastic model for this case is that the catheter describes a circular section of length s. This means that the exact shape of the catheter can be described as a parameterized curve with a form parameter $\alpha \in ]0, 2\pi]$ and the running parameter t (Equation 1):

$$(x; y)(t) = \left(\frac{s}{\alpha}(1 - \cos t); \frac{s}{\alpha} \sin t\right) mit \ t \in [0; \alpha]$$

The path length of this parameterized curve is always s which is already implicitly fulfilled.

The system of equations $$x_1 = f(1; a_1, \ldots, a_n).$$

$$\ldots$$

$$x_m = f(m; a_1, \ldots, a_n).$$

described above for the position of the sensor 3 corresponding to the tip of the catheter is then (Equation 2):

$$(x; y)_{S3} = \left(\frac{s}{\alpha}(1 - \cos \alpha); \frac{s}{\alpha} \sin \alpha\right)$$

In this example embodiment, α is proportional to and therefore indicates the curvature of the catheter and is generally a function of the value of the parameter (e.g. distance, force, stress, strain, and/or pressure) measured by the non-tracking sensor 8 and the material properties, particularly including the modulus of elasticity, and can be, in a first more specific example, proportional to the measured parameter indicative of a force (e.g. distance, force, stress, strain and/or pressure) divided by the modulus of elasticity or, in a second more specific example, proportional to the measured parameter indicative of a length (e.g. strain, distance) multiplied by the modulus of elasticity. The second sensor 440 measures one or more of a force applied to the tip of the elongate body relative to a proximal portion of the body by a force sensor, a pressure applied to the tip of the elongate body relative to a proximal portion of the body by a pressure sensor; and/or parameter a stress applied to the tip of the elongate body relative to a proximal portion of the body by a force sensor.

Figure 4:
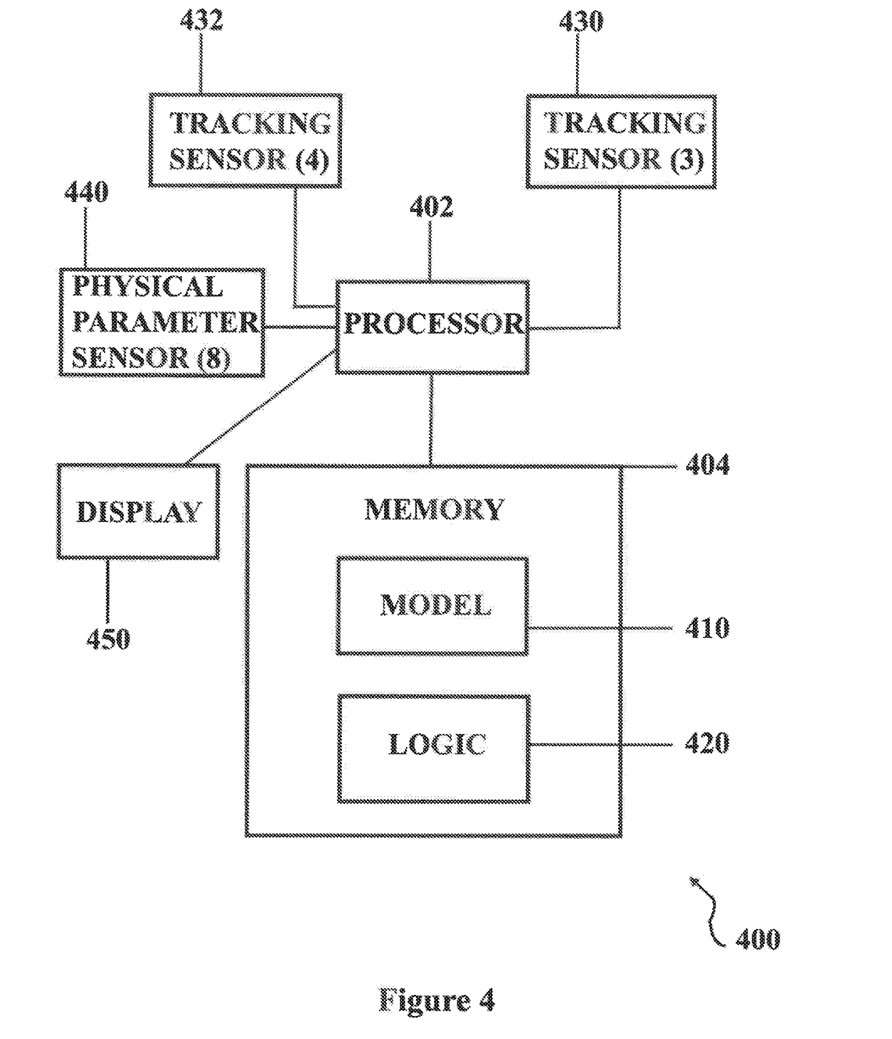
FIG. 4 is a schematic diagram showing a system in accordance with an example embodiment including a processor and a memory device operatively coupled with the processor for determining the spatial position and the shape of an elongated deformable body of an associated surgical instrument of the type shown in FIGS. 1 and 2.

FIG. 4 shows a schematic diagram of a system 400 in accordance with the example embodiments herein. The system 400 is shown without the surgical instrument 1 for ease of illustration only and, as shown, includes a processor 402 and a memory device 404 operatively coupled with the processor. The memory device may store information such as for example a predefined elasticity model 410. The memory devices may further store logic 420 that is executable by the processor to for determining the spatial position and the shape of an elongated deformable body of an associated surgical instrument.

In accordance with the example embodiment, the predefined elasticity model 410 stored in the memory device 404 describes deformation of the elongated deformable body of the associated surgical instrument as a function of a spatial position and orientation of a tip of the elongated deformable body of the associated surgical instrument relative to a mid-proximal location of the elongated deformable body spaced from the tip by a distance s along the body of the associated surgical instrument, and an influence on the elongated deformable body of the associated surgical instrument by at least one parameter.

A tracking sensor 430 is operatively coupled with the processor 402 in the system 400 of the example embodiment. Further in accordance with the example embodiment, the tracking sensor is physically disposed at the tip of the deformable body of the associated surgical instrument. The tracking sensor 430 determines a measured spatial position and orientation of the tip of the elongated deformable body relative to the mid-proximal location of the elongated deformable body.

A second tracking sensor 432 may be provided in an example embodiment such as, for example, in the system shown in FIG. 1. In this embodiment, the second tracking sensor 432 is operatively coupled with the processor 402 in the system 400 of the example embodiment. Further in accordance with the example embodiment, the second tracking sensor is physically disposed at a mid-proximal position of the deformable body of the associated surgical instrument. The second tracking sensor 432 is used together with the first tracking sensor 430 to determine a measured spatial position and orientation of the tip of the elongated deformable body relative to the mid-proximal location of the elongated deformable body.

The second tracking sensor may be replaced by and/or supplemented with a physical parameter sensor 440 operatively coupled with the processor 402 in the system 400 of a further example embodiment. Further in accordance with the example embodiment, the physical parameter sensor 440 is operatively coupled with the associated surgical instrument and is operable to determine the at least one parameter. The second sensor 440 measures one or more of a force applied to the tip of the elongate body relative to a proximal portion of the body by a force sensor, a pressure applied to the tip of the elongate body relative to a proximal portion of the body by a pressure sensor; and/or parameter a stress applied to the tip of the elongate body relative to a proximal portion of the body by a force sensor.

The logic 420 stored in the memory device 404 is executable by the processor 402 to calculate the spatial position and the shape of an elongated deformable body of an associated surgical instrument based on applying: i) the at least one parameter determined by the physical parameter sensor 440; and ii) the measured spatial position and orientation of the tip of the elongated deformable body relative to the mid-proximal location of the elongated deformable body determined by the tracking sensor 430 to the predefined elasticity model 410 of the elongated deformable body in the memory device.

The term "processor" as used herein refers to any microprocessor, discrete logic (e.g., ASIC), analog circuit, digital circuit, programmed logic device, memory device containing instructions, and so on. The term "processor" also refers to "logic" which may include one or more gates, combinations of gates, other circuit components, hardware, firmware, software in execution on a machine, and/or combinations of each to perform a function(s) or an action(s), and/or to cause a function or action from another logic, method, and/or system, a software controlled microprocessor, a discrete logic (e.g., ASIC), an analog circuit, a digital circuit, a programmed logic device, a memory device containing instructions, and so on. The term "memory" as used herein refers to any non-transitory media that participates in storing data and/or in providing instructions to the processor means for execution. Such a non-transitory medium may take many forms, including but not limited to volatile and non-volatile media. Non-volatile media includes, for example, optical or magnetic disks. Volatile media includes dynamic memory for example and does not include transitory signals, carrier waves, or the like. Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, or any other tangible non-transitory medium from which a computer can read.

It is to be understood that other embodiments will be utilized and structural and functional changes will be made without departing from the scope of the present invention. The foregoing descriptions of embodiments of the present invention have been presented for the purposes of illustration and description. It is not intended to be exhaustive or to limit the invention to the precise forms disclosed. Accordingly, many modifications and variations are possible in light of the above teachings. It is therefore intended that the scope of the invention be limited not by this detailed description.

It is now claimed:

1. A method in a system including a processor and a memory device operatively coupled with the processor for determining the spatial position and the shape of an elongated deformable body of an associated surgical instrument, the method comprising:
   storing a predefined elasticity model of the elongated deformable body in the memory device, wherein the predefined elasticity model describes deformation of the elongated deformable body of the associated surgical instrument as a function of:
      a spatial position and orientation of a tip of the elongated deformable body of the associated surgical instrument; and
      an influence on the elongated deformable body of the associated surgical instrument by at least one parameter;
   determining by a tracking sensor disposed at the tip of the deformable body of the associated surgical instrument, a measured spatial position and orientation of the tip of the elongated deformable body;
   determining the at least one parameter by a physical parameter sensor operatively coupled with the associated surgical instrument; and
   executing logic stored in the memory device to calculate the spatial position and the shape of an elongated deformable body of an associated surgical instrument based on applying: i) the at least one parameter determined by the physical parameter sensor; and ii) the measured spatial position and orientation of the tip of the elongated deformable body determined by the tracking sensor to the predefined elasticity model of the elongated deformable body in the memory device.

2. The method according to claim 1, wherein the determining the measured spatial position and orientation of the tip of the elongated deformable body comprises:
   determining the measured spatial position and orientation of the tip of the elongated deformable body by a tracking sensor disposed at the tip of the deformable body of the associated surgical instrument.

3. The method according to claim 2, wherein the determining the measured spatial position and orientation of the tip of the elongated deformable body comprises:
   determining the measured spatial position and orientation of the tip of the elongated deformable body by an electromagnetic (EM) tracking sensor tracking sensor disposed at the tip of the deformable body of the associated surgical instrument.

4. The method according to claim 3, wherein the determining the measured spatial position and orientation of the tip of the elongated deformable body comprises:
   determining the measured spatial position and orientation of the tip of the elongated deformable body by the EM tracking sensor using an EM tracking method.

5. The method according to claim 1, wherein the determining the at least one parameter comprises one or more of:
   determining as the at least one parameter a relative distance difference between a first portion of the deformable body on an outer side of a bend and a second portion of the deformable body opposite the first portion on the inner side of the bend by one or more distance sensors;
   determining as the at least one parameter a force applied to the tip of the elongate body relative to a proximal portion of the body by a force sensor;
   determining as the at least one parameter a pressure applied to the tip of the elongate body relative to a proximal portion of the body by a pressure sensor; and/or
   determining as the at least one parameter a stress applied to the tip of the elongate body relative to a proximal portion of the body by a force sensor.

6. The method according to claim 1, wherein the determining the measured spatial position and orientation of the tip of the elongated deformable body comprises:
   determining the measured spatial position and orientation of the tip of the elongated deformable body relative to the mid-proximal location of the elongated deformable body by determining a distance between a first tracking sensor disposed at the tip of the deformable body of the associated surgical instrument and a second tracking sensor disposed at the mid-proximal location of the elongated deformable body.

7. The method according to claim 1, wherein the elasticity model is over-determined by inputting the determined value of the at least one predetermined parameter and the determined spatial position and orientation of the tracking sensor.

8. The method according to claim 1 wherein the executing the logic stored in the memory device to calculate the spatial position and the shape of the elongated deformable body of the associated surgical instrument comprises:

executing finite element logic stored in the memory device to use a finite element method to calculate the spatial position and the shape of an elongated deformable body of an associated surgical instrument.

9. The method according to claim 1, wherein the determining the at least one parameter comprises:
   determining the at least one parameter by measuring a length of a pull-wire of a catheter which is pulled out of the proximal end of the catheter in order to change the shape of the catheter body so as to obtain information on the extent to which a deformable part of the catheter body will deform.

10. The method according to claim 1, wherein storing a predefined elasticity model of the elongated deformable body in the memory device comprises:
    acquiring a predefined elasticity model having a form comprising a running parameter t of:

$$(x; y)(t) = \left(\frac{s}{\alpha}(1 - \cos t); \frac{s}{\alpha}\sin t\right) mit\ t \in [0; \alpha]$$

wherein:
   the tracking sensor and the physical parameter sensor lie in a plane z=0 of an x, y, z, orthogonal coordinate space,
   the tracking sensor is in the coordinate origin and an axis of the physical parameter sensor is along the y axis of the x, y, z, orthogonal coordinate space,
   a portion of the associated surgical instrument between the tip of the elongated deformable body and the mid-proximal location of the elongated deformable body describes a circular section having a length s,
   an exact shape of the elongated deformable body of the associated surgical instrument is described as a parameterized curve with a form parameter $\alpha \in ]0, 2\pi]$ and with the running parameter t.

11. A surgical instrument comprising:
    an elongate flexible body;
    tracking sensor disposed at a tip of the deformable body, the tracking sensor determining a measured spatial position and orientation of the tip of the elongate flexible body; and
    a physical parameter sensor operatively coupled with the elongate flexible body, the physical parameter sensor determining at least one parameter of the elongate flexible body of the surgical instrument,
    wherein the spatial position and/or shape of the elongate flexible body is determinable using a predefined elasticity model of the elongate flexible body, wherein the predefined elasticity model describes deformation of the elongate flexible body of the surgical instrument as a function of:
      the measured spatial position and orientation of the tip of the elongated deformable body; and
      an influence on the elongate flexible body of the surgical instrument by the at least one parameter of the elongate flexible body of the surgical instrument.

12. The surgical instrument according to claim 11, wherein:
    the tracking sensor comprises an electromagnetic (EM) tracking sensor disposed at the tip of the elongate flexible body, the EM tracking sensor determining the measured spatial position and orientation of the tip of the elongate flexible body.

13. The surgical instrument according to claim 12, wherein:
    the physical parameter sensor comprises one or more of:
      a distance sensor determining as the at least one parameter a relative distance difference between a first portion of the elongate flexible body on an outer side of a bend and a second portion of the elongate flexible body opposite the first portion on the inner side of the bend;
      a force sensor determining as the at least one parameter a force applied to the tip of the elongate flexible body relative to a proximal portion of the elongate flexible body;
      a pressure sensor determining as the at least one parameter a pressure applied to the tip of the elongate flexible body relative to a proximal portion of the elongate flexible body; and/or
      a force sensor determining as the at least one parameter a stress applied to the tip of the elongate flexible body relative to a proximal portion of the elongate flexible body.

14. The surgical instrument according to claim 11, wherein:
    the physical parameter sensor comprises one or more of:
      a distance sensor determining as the at least one parameter a relative distance difference between a first portion of the elongate flexible body on an outer side of a bend and a second portion of the elongate flexible body opposite the first portion on the inner side of the bend;
      a force sensor determining as the at least one parameter a force applied to the tip of the elongate flexible body relative to a proximal portion of the elongate flexible body;
      a pressure sensor determining as the at least one parameter a pressure applied to the tip of the elongate flexible body relative to a proximal portion of the elongate flexible body; and/or
      a stress sensor determining as the at least one parameter a stress applied to the tip of the elongate flexible body relative to a proximal portion of the elongate flexible body.

15. The surgical instrument according to claim 11, further comprising:
    a pull-wire that is pullable from a proximal end of the surgical instrument in order to change the shape of the elongate flexible body,
    wherein the physical parameter sensor comprises a distance sensor determining a length of the pull-wire pulled from the proximal end of the surgical instrument as the at least one parameter.

16. The surgical instrument according to claim 11, further comprising:
    a pull-wire that is pullable from a proximal end of the surgical instrument in order to change the shape of the elongate flexible body,
    wherein the physical parameter sensor comprises a force sensor determining a forced used on the pull-wire as the at least one parameter.

17. The surgical instrument according to claim 11, wherein the predefined elasticity model describes the deformation of the elongate flexible body of the surgical instrument as a function of the measured spatial position and orientation of the tip of the elongate flexible body and the influence on the elongate flexible body of the surgical instrument by the at least one parameter of the elongate flexible body of the surgical instrument, and having a form comprising a running parameter t of:

$$(x; y)(t) = \left(\frac{s}{\alpha}(1 - \cos t); \frac{s}{\alpha}\sin t\right) mit\ t \in [0; \alpha]$$

wherein:
- the tracking sensor and the physical parameter sensor lie in a plane z=0 of an x, y, z, orthogonal coordinate space,
- the tracking sensor is in the coordinate origin and an axis of the physical parameter sensor is along the y axis of the x, y, z, orthogonal coordinate space,
- a portion of the associated surgical instrument between the tip of the elongate flexible body and the mid-proximal location of the elongate flexible body describes a circular section having a length s,
- an exact shape of the elongate flexible body of the associated surgical instrument is described as a parameterized curve with a form parameter $\alpha \in ]0, 2\pi]$ and with the running parameter t.

18. A system comprising:
- a surgical instrument comprising an elongate flexible body;
- a tracking sensor disposed at a tip of the elongate flexible body, the tracking sensor determining a measured spatial position and orientation of the tip of the elongate flexible body;
- a physical parameter sensor operatively coupled with the elongate flexible body, the physical parameter sensor determining at least one parameter of the elongate flexible body of the surgical instrument;
- a processor;
- a memory device operatively coupled with the processor;
- a predefined elasticity model of the elongate flexible body stored in the memory device, wherein the predefined elasticity model describes deformation of the elongate flexible body of the associated surgical instrument as a function of:
  - a spatial position and orientation of a tip of the elongate flexible body of the associated surgical instrument; and
  - an influence on the elongate flexible body of the associated surgical instrument by at least one parameter; and
- logic stored in the memory device, the logic being executable by the processor to calculate the spatial position and the shape of an elongate flexible body of an associated surgical instrument based on applying: i) the at least one parameter determined by the physical parameter sensor; and ii) the measured spatial position and orientation of the tip of the elongate flexible body determined by the tracking sensor to the predefined elasticity model of the elongate flexible body in the memory device.

19. The system according to claim 18, wherein:
- the tracking sensor comprises an electromagnetic (EM) tracking sensor disposed at the tip of the elongate flexible body, the EM tracking sensor determining the measured spatial position and orientation of the tip of the elongate flexible body; and
- the physical parameter sensor comprises one or more of:
  - a distance sensor determining as the at least one parameter a relative distance difference between a first portion of the elongate flexible body on an outer side of a bend and a second portion of the elongate flexible body opposite the first portion on the inner side of the bend;
  - a force sensor determining as the at least one parameter a force applied to the tip of the elongate flexible body relative to a proximal portion of the elongate flexible body;
  - a pressure sensor determining as the at least one parameter a pressure applied to the tip of the elongate flexible body relative to a proximal portion of the elongate flexible body; and/or
  - a force sensor determining as the at least one parameter a stress applied to the tip of the elongate flexible body relative to a proximal portion of the elongate flexible body.

20. The system according to claim 18, wherein the logic is executable by the processor to apply the predefined elasticity model having a form comprising a running parameter t of:

$$(x; y)(t) = \left(\frac{s}{\alpha}(1 - \cos t); \frac{s}{\alpha}\sin t\right) mit\ t \in [0; \alpha]$$

wherein:
- the tracking sensor and the physical parameter sensor lie in a plane z=0 of an x, y, z, orthogonal coordinate space,
- the tracking sensor is in the coordinate origin and an axis of the physical parameter sensor is along the y axis of the x, y, z, orthogonal coordinate space,
- a portion of the associated surgical instrument between the tip of the elongate flexible body and the mid-proximal location of the elongate flexible body describes a circular section having a length s,
- an exact shape of the elongate flexible body of the associated surgical instrument is described as a parameterized curve with a form parameter $\alpha \in ]0, 2\pi]$ and with the running parameter t.

* * * * *